United States Patent [19]

Mansour

[11] Patent Number: 5,583,011
[45] Date of Patent: Dec. 10, 1996

[54] COMPOSITIONS, TREATMENTS, AND DIAGNOSTICS FOR SCHISTOSOMIASIS AND RELATED DISEASES

[75] Inventor: Tag E. Mansour, Stanford, Calif.

[73] Assignee: Board of Trustees of the Leland Stanford University, Palo Alto, Calif.

[21] Appl. No.: 280,690

[22] Filed: Jul. 25, 1994

[51] Int. Cl.$^6$ ............................. C12P 21/06; C07H 21/04
[52] U.S. Cl. ....................... 435/69.1; 536/23.1; 536/23.2; 536/23.5; 536/24.3; 536/24.31; 935/14; 935/60
[58] Field of Search ................................. 536/23.1, 23.2, 536/23.5, 24.31, 24.5, 24.3; 935/14, 60; 435/69.1

[56] References Cited

PUBLICATIONS

T A Brown (1990) Gene Cloning pp. 153–177.
Cloning And Expression of a Human Muscle Phosphofructokinase cDNA, Sharma et al., Gene, vol. 77 (1989) 177–183.
Cloning of a cDNA Encoding Phosphofructokinase from *Haemonchus contorus*, Klein et al., M. and Biochem. Parasitology, vol. 48 (1991) 17–26.
Structure and Control of Phosphorfructokinase rom *Bacillus stearothermophilus*, Evans et al., Nature vol. 279 (1979) 500–504.
Crystal Structure of the Complex of Phorphofructokinase from *Escherichia coli* With its Reaction Products, Shirakihara et al., J. M. Biol. vol. 204 (1988) 973–994.
Evolution of Phospofructokinase—Gene Duplication and Creation of New Effector Cites, Poorman et al., Nature vol. 309 (1984) 467–469.

*Primary Examiner*—Bruce R. Campell
*Attorney, Agent, or Firm*—Cooley, Godward, Castro, Huddleson & Tatum

[57] ABSTRACT

Compositions and methods are provided for the detection and treatment of Schistosoma parasites. These compositions and methods are based on nucleic acid and amino acid sequences of Schistosoma phosphofructokinase.

21 Claims, 1 Drawing Sheet

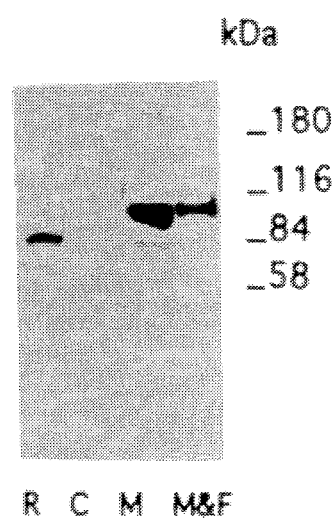

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 3047 base pairs
        ( B ) TYPE: nucleic acid
        ( C ) STRANDEDNESS: double
        ( D ) TOPOLOGY: unknown ( i i ) MOLECULE TYPE: cDNA ( i x ) FEATURE:
        ( A ) NAME/KEY: CDS
        ( B ) LOCATION: 147..2489

( x i ) SEQUENCE DESCRIPTION: SEQ ID NO:1:

```
CTGTTGTTTA TGGTATCTGT AGATTAACAC AACTAAAGGC TTCAAGTCAT CGTTTGGATT     60

TTCAGAAATA AAGCTTTGAC GTTTACTATT TGATAAACAT TCAGACACGA TATGGAATGT    120

AGAAGGTTTG AGCGCCGAGC AACAGA ATG GCT ACC TGG ATG GAA GGT AAA TAT    173
                             Met Ala Thr Trp Met Glu Gly Lys Tyr
                              1               5
```

| | | | | | | | | | | | | | | | | |
|---|---|---|---|---|---|---|---|---|---|---|---|---|---|---|---|---|
| GTT | GCC | CGA | GGA | CAA | TTT | ACG | GGT | GAA | TGT | ATC | GCT | GTT | CTT | ACG | AGC | 221 |
| Val | Ala | Arg | Gly | Gln | Phe | Thr | Gly | Glu | Cys | Ile | Ala | Val | Leu | Thr | Ser | |
| 10 | | | | 15 | | | | | 20 | | | | | | 25 | |
| GGT | GGA | GAT | GCA | CAA | GGA | ATG | AAT | GCA | GCT | GTA | CGA | GCT | GTA | GTC | CGT | 269 |
| Gly | Gly | Asp | Ala | Gln | Gly | Met | Asn | Ala | Ala | Val | Arg | Ala | Val | Val | Arg | |
| | | | | 30 | | | | | 35 | | | | | | 40 | |
| ATG | GGA | ATA | TAC | TGT | GGA | TGT | CGA | GTA | TTT | TTC | ATC | AGA | GAA | GGG | TAT | 317 |
| Met | Gly | Ile | Tyr | Cys | Gly | Cys | Arg | Val | Phe | Phe | Ile | Arg | Glu | Gly | Tyr | |
| | | | 45 | | | | | 50 | | | | | 55 | | | |
| CAA | GGT | CTT | GTG | GAT | GGT | GGT | CAA | AAC | ATT | CAG | GAG | GCA | TCG | TGG | GCA | 365 |
| Gln | Gly | Leu | Val | Asp | Gly | Gly | Gln | Asn | Ile | Gln | Glu | Ala | Ser | Trp | Ala | |
| | | | 60 | | | | | 65 | | | | | 70 | | | |
| GAC | GTC | TCT | GGT | ATT | CTC | CAA | TTG | GGA | GGT | ACT | AAG | ATT | GGG | TCA | GCT | 413 |
| Asp | Val | Ser | Gly | Ile | Leu | Gln | Leu | Gly | Gly | Thr | Lys | Ile | Gly | Ser | Ala | |
| | 75 | | | | | 80 | | | | | 85 | | | | | |
| CGA | TGT | ATG | GAT | TTT | CGT | GAA | CGT | TAT | GGA | CGT | TTA | AAA | GCT | GCT | GAA | 461 |
| Arg | Cys | Met | Asp | Phe | Arg | Glu | Arg | Tyr | Gly | Arg | Leu | Lys | Ala | Ala | Glu | |
| 90 | | | | | 95 | | | | | 100 | | | | | 105 | |
| AAT | CTA | GTC | AAA | AAT | CAA | ATA | ACC | AAT | TTA | GTG | GTT | ATT | GGC | GGT | GAT | 509 |
| Asn | Leu | Val | Lys | Asn | Gln | Ile | Thr | Asn | Leu | Val | Val | Ile | Gly | Gly | Asp | |
| | | | | 110 | | | | | 115 | | | | | 120 | | |
| GGT | TCT | TTA | ACT | GGT | GCT | AAT | CTA | TTT | CGA | GCT | GAA | TGG | TCA | AGT | CTA | 557 |
| Gly | Ser | Leu | Thr | Gly | Ala | Asn | Leu | Phe | Arg | Ala | Glu | Trp | Ser | Ser | Leu | |
| | | | 125 | | | | | 130 | | | | | 135 | | | |
| TTG | GAA | GAA | CTT | GTC | ACA | TCA | AAT | AAA | ATT | AGT | GCA | GAA | AGT | GCC | AAA | 605 |
| Leu | Glu | Glu | Leu | Val | Thr | Ser | Asn | Lys | Ile | Ser | Ala | Glu | Ser | Ala | Lys | |
| | | | 140 | | | | | 145 | | | | | 150 | | | |
| CAA | TTT | CAT | CGT | TTA | AAT | ATT | GTC | GGT | TTA | GTC | GGT | AGT | ATT | GAC | AAT | 653 |
| Gln | Phe | His | Arg | Leu | Asn | Ile | Val | Gly | Leu | Val | Gly | Ser | Ile | Asp | Asn | |
| | 155 | | | | | 160 | | | | | 165 | | | | | |
| GAT | TTT | TGT | GGT | ACA | GAT | ATG | ACA | ATT | GGT | GCA | GAC | TCA | GCA | TTG | CAT | 701 |
| Asp | Phe | Cys | Gly | Thr | Asp | Met | Thr | Ile | Gly | Ala | Asp | Ser | Ala | Leu | His | |
| 170 | | | | | 175 | | | | | 180 | | | | | 185 | |
| AGA | ATT | ATT | GAA | GCG | ACT | GAT | GCA | ATC | TCT | ACT | ACA | GCT | CAC | TCA | CAT | 749 |
| Arg | Ile | Ile | Glu | Ala | Thr | Asp | Ala | Ile | Ser | Thr | Thr | Ala | His | Ser | His | |
| | | | | 190 | | | | | 195 | | | | | 200 | | |
| CAA | AGA | TGT | TTC | ATT | TTA | GAG | GTG | ATG | GGT | AGA | CAT | TGT | GGC | TAT | CTA | 797 |
| Gln | Arg | Cys | Phe | Ile | Leu | Glu | Val | Met | Gly | Arg | His | Cys | Gly | Tyr | Leu | |
| | | | 205 | | | | | 210 | | | | | 215 | | | |
| GCA | CTT | GTC | GCA | TCT | ATG | GCG | TGT | GAA | GCT | GAT | TGG | GTA | TTT | ATA | CCA | 845 |
| Ala | Leu | Val | Ala | Ser | Met | Ala | Cys | Glu | Ala | Asp | Trp | Val | Phe | Ile | Pro | |
| | | 220 | | | | | 225 | | | | | 230 | | | | |
| GAA | ATG | CCA | CCA | ACT | GAT | GAT | TGG | CGT | GAA | AAA | TTA | TGT | CAT | AAA | CTT | 893 |
| Glu | Met | Pro | Pro | Thr | Asp | Asp | Trp | Arg | Glu | Lys | Leu | Cys | His | Lys | Leu | |
| | 235 | | | | | 240 | | | | | 245 | | | | | |
| CGA | ATG | AAT | CGT | GAA | CAT | GGA | CAA | CGT | GTC | AAT | ATA | ATT | ATG | GTT | GCT | 941 |
| Arg | Met | Asn | Arg | Glu | His | Gly | Gln | Arg | Val | Asn | Ile | Ile | Met | Val | Ala | |
| 250 | | | | | 255 | | | | | 260 | | | | | 265 | |
| GAA | GGT | GCT | ATC | GAT | AGA | GCA | TGT | AAA | CCG | ATC | ACT | TGT | GAA | ATA | GTG | 989 |
| Glu | Gly | Ala | Ile | Asp | Arg | Ala | Cys | Lys | Pro | Ile | Thr | Cys | Glu | Ile | Val | |
| | | | | 270 | | | | | 275 | | | | | 280 | | |
| AAA | AAT | TTA | ATA | GTA | TCA | GAA | CTT | CAA | CTT | GAT | ACA | CGT | ATA | ACT | GTT | 1037 |
| Lys | Asn | Leu | Ile | Val | Ser | Glu | Leu | Gln | Leu | Asp | Thr | Arg | Ile | Thr | Val | |

|  |  |  |  |  |  | 285 |  |  |  |  |  | 290 |  |  |  |  |  | 295 |  |  |  |
|---|---|---|---|---|---|---|---|---|---|---|---|---|---|---|---|---|---|---|---|---|---|---|
| TTG | GGT | CAT | GTC | CAA | CGT | GGT | GGT | TCA | CCA | TCT | GCA | TTT | GAT | CGT | ATT | | | | | | | 1085 |
| Leu | Gly | His 300 | Val | Gln | Arg | Gly | Gly 305 | Ser | Pro | Ser | Ala | Phe 310 | Asp | Arg | Ile | | | | | | | |
| TTG | GGC | AGT | CGT | ATG | GGA | GCT | GAA | GCT | GTT | CTA | GCC | CTA | ATG | GAT | GCT | | | | | | | 1133 |
| Leu | Gly | Ser 315 | Arg | Met | Gly | Ala | Glu 320 | Ala | Val | Leu | Ala | Leu 325 | Met | Asp | Ala | | | | | | | |
| GAT | CGT | GAT | CCT | AAT | CTA | CCA | TCA | TGT | GTT | ATT | AGT | TTG | GAT | GGT | AAC | | | | | | | 1181 |
| Asp 330 | Arg | Asp | Pro | Asn | Leu 335 | Pro | Ser | Cys | Val | Ile 340 | Ser | Leu | Asp | Gly | Asn 345 | | | | | | | |
| CAA | GCA | GTT | CGT | GTA | CCA | CTT | GTG | AAA | TGT | GTT | GAC | AGA | ACA | CGT | CAG | | | | | | | 1229 |
| Gln | Ala | Val | Arg | Val 350 | Pro | Leu | Val | Lys | Cys 355 | Val | Asp | Arg | Thr | Arg 360 | Gln | | | | | | | |
| GTT | GCT | GAA | GCA | ATG | AAA | GCT | TGT | GAT | TTT | GAT | CAT | GCC | GTT | GAA | CTA | | | | | | | 1277 |
| Val | Ala | Glu | Ala 365 | Met | Lys | Ala | Cys | Asp 370 | Phe | Asp | His | Ala | Val 375 | Glu | Leu | | | | | | | |
| CGT | GGA | ACG | AGT | TTC | ATG | AAC | AAT | TTA | GCA | ACG | TAT | ATA | AAA | CTT | TCA | | | | | | | 1325 |
| Arg | Gly | Thr 380 | Ser | Phe | Met | Asn | Asn 385 | Leu | Ala | Thr | Tyr | Ile 390 | Lys | Leu | Ser | | | | | | | |
| AAA | ATT | GAA | CAA | CCA | CGT | CAA | AGT | GTC | ATG | TCA | TCT | GAA | AAC | AAC | TTG | | | | | | | 1373 |
| Lys | Ile 395 | Glu | Gln | Pro | Arg | Gln 400 | Ser | Val | Met | Ser | Ser 405 | Glu | Asn | Asn | Leu | | | | | | | |
| AGA | ATC | GGT | ATC | GTG | AAT | GTC | GGT | GCT | CCA | GCT | TGC | GGT | ATT | AAT | GCA | | | | | | | 1421 |
| Arg 410 | Ile | Gly | Ile | Val | Asn 415 | Val | Gly | Ala | Pro | Ala 420 | Cys | Gly | Ile | Asn | Ala 425 | | | | | | | |
| GTA | ATA | AGA | GGA | TTT | ACT | CGT | TTG | GGT | ATC | ACT | AAA | GGT | TAT | AAG | GTT | | | | | | | 1469 |
| Val | Ile | Arg | Gly | Phe 430 | Thr | Arg | Leu | Gly | Ile 435 | Thr | Lys | Gly | Tyr | Lys 440 | Val | | | | | | | |
| ATC | GGA | ATA | CAC | GAA | GGA | TTT | TCC | GGG | CTT | GTT | AAA | GGT | GAT | GCT | AGT | | | | | | | 1517 |
| Ile | Gly | Ile | His 445 | Glu | Gly | Phe | Ser | Gly 450 | Leu | Val | Lys | Gly | Asp 455 | Ala | Ser | | | | | | | |
| GAA | ATA | CAG | TGG | GCT | GAT | GTC | CGT | GGA | TGG | GTG | GGA | ATG | GGT | GGT | TCT | | | | | | | 1565 |
| Glu | Ile | Gln 460 | Trp | Ala | Asp | Val | Arg 465 | Gly | Trp | Val | Gly | Met 470 | Gly | Gly | Ser | | | | | | | |
| ATG | TTA | GGA | ACA | CGT | AGA | GAT | ACA | CCG | AAT | GGT | TTG | GGT | ATA | GAT | AAA | | | | | | | 1613 |
| Met | Leu 475 | Gly | Thr | Arg | Arg | Asp 480 | Thr | Pro | Asn | Gly | Leu 485 | Gly | Ile | Asp | Lys | | | | | | | |
| GTA | GCG | GCG | AAA | TTT | AAA | GAA | TTA | AAA | TTA | AGT | GGT | CTA | CTT | ATT | ATT | | | | | | | 1661 |
| Val 490 | Ala | Ala | Lys | Phe | Lys 495 | Glu | Leu | Lys | Leu | Ser 500 | Gly | Leu | Leu | Ile | Ile 505 | | | | | | | |
| GGT | GGC | TTT | GAA | GCG | TAC | GAA | TGT | ATG | ATA | GAA | CTG | GTT | GAA | GGA | CGT | | | | | | | 1709 |
| Gly | Gly | Phe | Glu | Ala 510 | Tyr | Glu | Cys | Met | Ile 515 | Glu | Leu | Val | Glu | Gly 520 | Arg | | | | | | | |
| GAA | AAA | TAT | CCT | GAA | TTA | TGT | ATA | CCT | ATG | GCT | ATG | GTA | CCA | GCG | ACA | | | | | | | 1757 |
| Glu | Lys | Tyr | Pro 525 | Glu | Leu | Cys | Ile | Pro 530 | Met | Ala | Met | Val | Pro 535 | Ala | Thr | | | | | | | |
| ATT | TCT | AAT | AAT | GTT | CCT | GGT | ACT | GAT | TTC | TCT | TTG | GGT | TGT | GAT | ACA | | | | | | | 1805 |
| Ile | Ser | Asn 540 | Asn | Val | Pro | Gly | Thr 545 | Asp | Phe | Ser | Leu | Gly 550 | Cys | Asp | Thr | | | | | | | |
| GCT | TTA | AAT | GAA | ATA | ACC | TCT | GTT | TTA | GAT | AAA | ATT | AAA | CAA | AGT | GCA | | | | | | | 1853 |
| Ala | Leu | Asn 555 | Glu | Ile | Thr | Ser | Val 560 | Leu | Asp | Lys | Ile | Lys 565 | Gln | Ser | Ala | | | | | | | |
| TTA | GGT | ACA | AAA | CGT | CGT | GTA | TTT | GTT | GTT | GAA | ACA | ATG | GGC | GGT | TAT | | | | | | | 1901 |
| Leu 570 | Gly | Thr | Lys | Arg | Arg 575 | Val | Phe | Val | Val | Glu 580 | Thr | Met | Gly | Gly | Tyr 585 | | | | | | | |
| TGT | GGT | TAT | TTA | GCT | ACA | ATG | AGT | GCA | TTG | GCT | GGT | GGA | GCA | GAT | GCT | | | | | | | 1949 |
| Cys | Gly | Tyr | Leu | Ala 590 | Thr | Met | Ser | Ala | Leu 595 | Ala | Gly | Gly | Ala | Asp 600 | Ala | | | | | | | |
| GCT | TAT | ATA | TTT | GAA | GAA | CCA | TTT | ACA | ATT | GAT | GAT | TTA | CGT | GAA | GAT | | | | | | | 1997 |
| Ala | Tyr | Ile | Phe | Glu | Glu | Pro | Phe | Thr | Ile | Asp | Asp | Leu | Arg | Glu | Asp | | | | | | | |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     | 605 |     |     |     |     | 610 |     |     |     |     | 615 |     |      |
| GTA | GTA | CAT | TTA | CGT | GCA | AAA | ATT | GAT | GAT | AAT | GTT | AAA | CGT | GGT | TTA | 2045 |
| Val | Val | His | Leu | Arg | Ala | Lys | Ile | Asp | Asp | Asn | Val | Lys | Arg | Gly | Leu |      |
|     |     | 620 |     |     |     |     | 625 |     |     |     |     |     | 630 |     |     |      |
| GTA | CTA | CGA | GCT | GAT | ATG | CTA | ATA | AAT | ACT | ATA | ACA | AGT | GAA | TTT | ATT | 2093 |
| Val | Leu | Arg | Ala | Asp | Met | Leu | Ile | Asn | Thr | Ile | Thr | Ser | Glu | Phe | Ile |      |
|     | 635 |     |     |     |     | 640 |     |     |     |     | 645 |     |     |     |     |      |
| CAT | CAA | TTA | TAT | GCT | CAA | GAA | GGT | CAA | GGT | ATA | TTT | GAT | TGC | CGT | TGT | 2141 |
| His | Gln | Leu | Tyr | Ala | Gln | Glu | Gly | Gln | Gly | Ile | Phe | Asp | Cys | Arg | Cys |      |
| 650 |     |     |     |     | 655 |     |     |     |     | 660 |     |     |     |     | 665 |      |
| AAT | GTA | CTA | GGT | CAT | ATG | CAA | CAA | GGT | GAT | AGA | CCA | AGT | CCA | TTT | GAT | 2189 |
| Asn | Val | Leu | Gly | His | Met | Gln | Gln | Gly | Asp | Arg | Pro | Ser | Pro | Phe | Asp |      |
|     |     |     |     | 670 |     |     |     |     | 675 |     |     |     |     | 680 |     |      |
| AGA | AGT | TTA | GGT | ACA | AAA | TTT | GCA | TCG | AAA | GCA | ATT | GAC | TGG | TTA | GAC | 2237 |
| Arg | Ser | Leu | Gly | Thr | Lys | Phe | Ala | Ser | Lys | Ala | Ile | Asp | Trp | Leu | Asp |      |
|     |     |     | 685 |     |     |     |     | 690 |     |     |     |     | 695 |     |     |      |
| GAA | CAA | ATC | AAC | GCT | AAT | ATC | GTT | CAG | ATT | CTA | CAG | TCT | ATA | CAC | CAG | 2285 |
| Glu | Gln | Ile | Asn | Ala | Asn | Ile | Val | Gln | Ile | Leu | Gln | Ser | Ile | His | Gln |      |
|     |     | 700 |     |     |     |     | 705 |     |     |     |     | 710 |     |     |     |      |
| ACA | TTT | ATG | TTG | TAC | ATT | AAT | TGG | TAT | TGT | ACG | TCG | TCA | GAC | AAC | TTA | 2333 |
| Thr | Phe | Met | Leu | Tyr | Ile | Asn | Trp | Tyr | Cys | Thr | Ser | Ser | Asp | Asn | Leu |      |
|     | 715 |     |     |     |     | 720 |     |     |     |     | 725 |     |     |     |     |      |
| TTC | AAA | TAT | TCA | CTG | GAA | TTA | AGA | GAA | CAT | ACA | GAT | TTC | GTA | CAT | CGT | 2381 |
| Phe | Lys | Tyr | Ser | Leu | Glu | Leu | Arg | Glu | His | Thr | Asp | Phe | Val | His | Arg |      |
| 730 |     |     |     |     | 735 |     |     |     |     | 740 |     |     |     |     | 745 |      |
| TTA | CCA | AAA | GAA | GAA | TGG | TGG | CTT | AGT | TTA | CGT | CCA | TTA | ATG | CGT | ATT | 2429 |
| Leu | Pro | Lys | Glu | Glu | Trp | Trp | Leu | Ser | Leu | Arg | Pro | Leu | Met | Arg | Ile |      |
|     |     |     |     | 750 |     |     |     |     | 755 |     |     |     |     | 760 |     |      |
| ATG | GCT | AAA | CAT | GAT | AGT | CTT | TAT | GAA | TCA | GAA | AGT | ATT | ATG | GCT | GGT | 2477 |
| Met | Ala | Lys | His | Asp | Ser | Leu | Tyr | Glu | Ser | Glu | Ser | Ile | Met | Ala | Gly |      |
|     |     | 765 |     |     |     |     | 770 |     |     |     |     | 775 |     |     |     |      |
| ACT | GAT | AGA | AAA | TAATTACTTT | TTCTTTATC | ATACATATTT | CAACTTATTC |     |     |     |     |     |     |     |     | 2529 |
| Thr | Asp | Arg | Lys |     |     |     |     |     |     |     |     |     |     |     |     |      |
|     |     |     | 780 |     |     |     |     |     |     |     |     |     |     |     |     |      |

```
AATATTAGTT  TTGCTTAATT  TTCATTCATA  AAATCAGATC  TTATTATTAT  TGTTAATATC   2589
GATAATTTTT  TTGTCTTTTT  CTTGTTGTTT  TCTTCACTGA  TTTATTCGTT  TACTTAGTTA   2649
CTACTTATGG  TAATTCAACC  AACCTTGTCC  ATCTTATTCT  GCTTTATTGA  AGATTAATCA   2709
ATAATATGTA  TTGTAACCCT  ACAAGTTTAG  TTAAATTCAA  TATTATAAAT  CAGTCATTTT   2769
AACCTTTCAA  AACCAACACC  GATCGCCTTT  ACTATAGTTG  TAGAAAATGA  AATTTAATTT   2829
AGCCCTTTTT  TTTCAAGAAA  AAAAAGGAGA  AAAACAAAGT  AAAGAAAAAC  GAAAGTATT    2889
GCTAACATGT  TCCTTTCATT  CTGTTTTTTT  TTCCTTTTTT  TGTCTTTTAG  TGAGGGTATG   2949
TAGTATTGTC  CTAGTGCAAT  ATTTAAAGTT  TTGTCATGTT  TTCCGTTTTT  TTTTTGTACA   3009
ACAGAGAAAT  TATATAATAA  ACACTTTGAT  TTTCATGT                             3047
```

( 2 ) INFORMATION FOR SEQ ID NO:2:

( i ) SEQUENCE CHARACTERISTICS:
        ( A ) LENGTH: 781 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Ala  Thr  Trp  Met  Glu  Gly  Lys  Tyr  Val  Ala  Arg  Gly  Gln  Phe  Thr
 1             5                    10                           15

Gly  Glu  Cys  Ile  Ala  Val  Leu  Thr  Ser  Gly  Gly  Asp  Ala  Gln  Gly  Met
```

|  |  |  | 20 |  |  |  | 25 |  |  |  | 30 |  |
|---|---|---|---|---|---|---|---|---|---|---|---|---|
| Asn | Ala | Ala | Val | Arg | Ala | Val | Val | Arg | Met | Gly | Ile | Tyr | Cys | Gly | Cys |
|  |  | 35 |  |  |  | 40 |  |  |  |  | 45 |  |
| Arg | Val | Phe | Phe | Ile | Arg | Glu | Gly | Tyr | Gln | Gly | Leu | Val | Asp | Gly | Gly |
|  | 50 |  |  |  | 55 |  |  |  |  | 60 |  |  |
| Gln | Asn | Ile | Gln | Glu | Ala | Ser | Trp | Ala | Asp | Val | Ser | Gly | Ile | Leu | Gln |
| 65 |  |  |  | 70 |  |  |  |  | 75 |  |  |  |  | 80 |
| Leu | Gly | Gly | Thr | Lys | Ile | Gly | Ser | Ala | Arg | Cys | Met | Asp | Phe | Arg | Glu |
|  |  |  | 85 |  |  |  |  | 90 |  |  |  |  | 95 |
| Arg | Tyr | Gly | Arg | Leu | Lys | Ala | Ala | Glu | Asn | Leu | Val | Lys | Asn | Gln | Ile |
|  |  |  | 100 |  |  |  | 105 |  |  |  | 110 |  |
| Thr | Asn | Leu | Val | Val | Ile | Gly | Gly | Asp | Gly | Ser | Leu | Thr | Gly | Ala | Asn |
|  |  | 115 |  |  |  | 120 |  |  |  |  | 125 |  |
| Leu | Phe | Arg | Ala | Glu | Trp | Ser | Ser | Leu | Leu | Glu | Glu | Leu | Val | Thr | Ser |
|  | 130 |  |  |  | 135 |  |  |  |  | 140 |  |  |
| Asn | Lys | Ile | Ser | Ala | Glu | Ser | Ala | Lys | Gln | Phe | His | Arg | Leu | Asn | Ile |
| 145 |  |  |  |  | 150 |  |  |  |  | 155 |  |  |  | 160 |
| Val | Gly | Leu | Val | Gly | Ser | Ile | Asp | Asn | Asp | Phe | Cys | Gly | Thr | Asp | Met |
|  |  |  | 165 |  |  |  | 170 |  |  |  |  | 175 |
| Thr | Ile | Gly | Ala | Asp | Ser | Ala | Leu | His | Arg | Ile | Ile | Glu | Ala | Thr | Asp |
|  |  | 180 |  |  |  |  | 185 |  |  |  |  | 190 |  |
| Ala | Ile | Ser | Thr | Thr | Ala | His | Ser | His | Gln | Arg | Cys | Phe | Ile | Leu | Glu |
|  | 195 |  |  |  |  | 200 |  |  |  |  | 205 |  |
| Val | Met | Gly | Arg | His | Cys | Gly | Tyr | Leu | Ala | Leu | Val | Ala | Ser | Met | Ala |
|  | 210 |  |  |  | 215 |  |  |  |  | 220 |  |  |
| Cys | Glu | Ala | Asp | Trp | Val | Phe | Ile | Pro | Glu | Met | Pro | Pro | Thr | Asp | Asp |
| 225 |  |  |  |  | 230 |  |  |  |  | 235 |  |  |  | 240 |
| Trp | Arg | Glu | Lys | Leu | Cys | His | Lys | Leu | Arg | Met | Asn | Arg | Glu | His | Gly |
|  |  |  | 245 |  |  |  |  | 250 |  |  |  |  | 255 |
| Gln | Arg | Val | Asn | Ile | Ile | Met | Val | Ala | Glu | Gly | Ala | Ile | Asp | Arg | Ala |
|  |  |  | 260 |  |  |  | 265 |  |  |  | 270 |  |
| Cys | Lys | Pro | Ile | Thr | Cys | Glu | Ile | Val | Lys | Asn | Leu | Ile | Val | Ser | Glu |
|  |  | 275 |  |  |  | 280 |  |  |  |  | 285 |  |
| Leu | Gln | Leu | Asp | Thr | Arg | Ile | Thr | Val | Leu | Gly | His | Val | Gln | Arg | Gly |
|  | 290 |  |  |  | 295 |  |  |  |  | 300 |  |  |
| Gly | Ser | Pro | Ser | Ala | Phe | Asp | Arg | Ile | Leu | Gly | Ser | Arg | Met | Gly | Ala |
| 305 |  |  |  | 310 |  |  |  |  | 315 |  |  |  |  | 320 |
| Glu | Ala | Val | Leu | Ala | Leu | Met | Asp | Ala | Asp | Arg | Asp | Pro | Asn | Leu | Pro |
|  |  |  |  | 325 |  |  |  | 330 |  |  |  |  | 335 |
| Ser | Cys | Val | Ile | Ser | Leu | Asp | Gly | Asn | Gln | Ala | Val | Arg | Val | Pro | Leu |
|  |  |  | 340 |  |  |  | 345 |  |  |  |  | 350 |
| Val | Lys | Cys | Val | Asp | Arg | Thr | Arg | Gln | Val | Ala | Glu | Ala | Met | Lys | Ala |
|  |  | 355 |  |  |  |  | 360 |  |  |  |  | 365 |  |
| Cys | Asp | Phe | Asp | His | Ala | Val | Glu | Leu | Arg | Gly | Thr | Ser | Phe | Met | Asn |
|  | 370 |  |  |  |  | 375 |  |  |  |  | 380 |  |
| Asn | Leu | Ala | Thr | Tyr | Ile | Lys | Leu | Ser | Lys | Ile | Glu | Gln | Pro | Arg | Gln |
| 385 |  |  |  |  | 390 |  |  |  |  | 395 |  |  |  | 400 |
| Ser | Val | Met | Ser | Ser | Glu | Asn | Asn | Leu | Arg | Ile | Gly | Ile | Val | Asn | Val |
|  |  |  |  | 405 |  |  |  |  | 410 |  |  |  |  | 415 |
| Gly | Ala | Pro | Ala | Cys | Gly | Ile | Asn | Ala | Val | Ile | Arg | Gly | Phe | Thr | Arg |
|  |  |  | 420 |  |  |  | 425 |  |  |  |  | 430 |
| Leu | Gly | Ile | Thr | Lys | Gly | Tyr | Lys | Val | Ile | Gly | Ile | His | Glu | Gly | Phe |
|  |  | 435 |  |  |  |  | 440 |  |  |  |  | 445 |

| | | | | | | | | | | | | | | |
|---|---|---|---|---|---|---|---|---|---|---|---|---|---|---|
| Ser | Gly 450 | Leu | Val | Lys | Gly | Asp 455 | Ala | Ser | Glu | Ile | Gln 460 | Trp | Ala | Asp | Val |
| Arg 465 | Gly | Trp | Val | Gly | Met 470 | Gly | Gly | Ser | Met | Leu 475 | Gly | Thr | Arg | Arg | Asp 480 |
| Thr | Pro | Asn | Gly | Leu 485 | Gly | Ile | Asp | Lys | Val 490 | Ala | Ala | Lys | Phe | Lys 495 | Glu |
| Leu | Lys | Leu | Ser 500 | Gly | Leu | Leu | Ile | Ile 505 | Gly | Gly | Phe | Glu | Ala 510 | Tyr | Glu |
| Cys | Met | Ile 515 | Glu | Leu | Val | Glu | Gly 520 | Arg | Glu | Lys | Tyr | Pro 525 | Glu | Leu | Cys |
| Ile | Pro 530 | Met | Ala | Met | Val | Pro 535 | Ala | Thr | Ile | Ser | Asn 540 | Asn | Val | Pro | Gly |
| Thr 545 | Asp | Phe | Ser | Leu | Gly 550 | Cys | Asp | Thr | Ala | Leu 555 | Asn | Glu | Ile | Thr | Ser 560 |
| Val | Leu | Asp | Lys | Ile 565 | Lys | Gln | Ser | Ala | Leu 570 | Gly | Thr | Lys | Arg | Arg 575 | Val |
| Phe | Val | Val | Glu 580 | Thr | Met | Gly | Gly | Tyr 585 | Cys | Gly | Tyr | Leu | Ala 590 | Thr | Met |
| Ser | Ala | Leu 595 | Ala | Gly | Gly | Ala | Asp 600 | Ala | Ala | Tyr | Ile | Phe 605 | Glu | Glu | Pro |
| Phe | Thr 610 | Ile | Asp | Asp | Leu | Arg 615 | Glu | Asp | Val | Val | His 620 | Leu | Arg | Ala | Lys |
| Ile 625 | Asp | Asp | Asn | Val | Lys 630 | Arg | Gly | Leu | Val | Leu 635 | Arg | Ala | Asp | Met | Leu 640 |
| Ile | Asn | Thr | Ile | Thr 645 | Ser | Glu | Phe | Ile | His 650 | Gln | Leu | Tyr | Ala | Gln 655 | Glu |
| Gly | Gln | Gly | Ile 660 | Phe | Asp | Cys | Arg | Cys 665 | Asn | Val | Leu | Gly | His 670 | Met | Gln |
| Gln | Gly | Asp 675 | Arg | Pro | Ser | Pro | Phe 680 | Asp | Arg | Ser | Leu | Gly 685 | Thr | Lys | Phe |
| Ala | Ser 690 | Lys | Ala | Ile | Asp | Trp 695 | Leu | Asp | Glu | Gln | Ile 700 | Asn | Ala | Asn | Ile |
| Val 705 | Gln | Ile | Leu | Gln | Ser 710 | Ile | His | Gln | Thr | Phe 715 | Met | Leu | Tyr | Ile | Asn 720 |
| Trp | Tyr | Cys | Thr | Ser 725 | Ser | Asp | Asn | Leu | Phe 730 | Lys | Tyr | Ser | Leu | Glu 735 | Leu |
| Arg | Glu | His | Thr 740 | Asp | Phe | Val | His | Arg 745 | Leu | Pro | Lys | Glu | Glu 750 | Trp | Trp |
| Leu | Ser | Leu 755 | Arg | Pro | Leu | Met | Arg 760 | Ile | Met | Ala | Lys | His 765 | Asp | Ser | Leu |
| Tyr | Glu 770 | Ser | Glu | Ser | Ile | Met 775 | Ala | Gly | Thr | Asp | Arg 780 | Lys | | | |

COMPOSITIONS, TREATMENTS, AND DIAGNOSTICS FOR SCHISTOSOMIASIS AND RELATED DISEASES

ACKNOWLEDGEMENTS

This invention was made with government support under contract AI16501 awarded by the National Institutes of Health. The Government has certain rights in this invention.

INTRODUCTION

1. Technical Field

This invention relates to compounds and methods for the treatment and detection of trematodes, in particular trematodes of the genus Schistosoma.

2. Background

Parasitic worms of the genus Schismsoma cause Schistosomiasis in humans. These parasites infect some 220 million people, mostly in developing countries, and are the cause of considerable morbidity and mortality. Although adult schistosomes live in an aerobic environment, they depend on anaerobic glycolysis for their energy metabolism (Bueding, E. (1950) J. Gem Physiol. 33, 475–495). Glucose is metabolized and excreted almost quantitatively as lactic acid by schistosomes. Phosphofructokinase (herein referred to as "PFK") (ATP:D-fructose-6-phosphate-1phosphotransferase, EC 2.7.1.11) limits the rate of glycolysis in these parasites (Mansour, T. E. and Bueding, E. (1954) Br. J. Pharmacol. 9, 459–462; Bueding, E. and Mansour, J. M. (1957) Br. J. Pharmacol. 12, 159–165).

Schistosoma infections are typically treated with antimony compounds. Because of PFK's critical role in the regulation of energy metabolism in schistosomes it has been postulated that phosphofructokinase is a possible target for antischistosomal agents, e.g., antimonials (Mansour, T. E. and Bueding, E. (1954) Br. J. Pharmacol. 9, 459–462; Bueding, E. and Mansour, J. M. (1957) Br. J. Pharmacol. 12, 159–165; Mansour, T. E. (1979)Science 205, 462–269).

Although the biochemical properties of Schistosoma PFK are not well defined, PFK's from the genus Schistosoma and related parasite genus Fasciola, have been found to possess biochemical properties significantly different from mammalian host PFK. Parasite PFK is more sensitive to inhibition by antischistosomal antimonials than mammalian host PFK (Bueding, E. and Mansour, J. M. (1957) Br. J. Pharmacol. 12, 159–165). Parasite PFK undergoes regulatory phosphorylation unlike mammalian host PFK. Phosphofructokinase in this class of parasites is regulated by serotonin receptors that are linked to a GTP-binding protein and an adenylate cyclase/protein kinase phosphorylation system (Mansour, T. E. and Mansour, J. M. (1962) J. Biol. Chem. 237, 629–634; Iitzsch, M. I., Bieber, D., Vijayasavathy, S., Webster, P., Zurita, M., Ding, J., and Mansour, T. E. (1992) J. Biol. Chem. 267, 14504–14508; Kamemoto, E. S. and Mansour, T. E. (1986)J. Biol. Chem. 261, 4346–4351; Estey, S. J. and Mansour, T. E. (1987) Mol. Biochem. Parasitol. 26, 47–60; Kamemoto, E. S., Lan, L. and Mansour, T. E. (1989) Arch Biochem. Biophys. 271,553–559).

Although the demonstration of PFK as a selective drug target in Schistosoma mansoni was reported in the fifties, enzymological studies on the nature of the enzyme have been hampered by the unavailability of sufficient parasite material to isolate highly pure enzyme (Mansour, T. E. and Bueding, E. (1954) Br. J. Pharmacol. 9, 459–462; Bueding, E. and Mansour, J. M. (1957) Br. J. Pharmacol. 12, 159–165). PFK structure/function relationships have been elucidated largely from crystallographic analysis of the enzymes from Bacillus stearothermophilus and E. Coli (Evans, P. R. and Hudson, P. J. (1979) Nature 279, 500–504; Shirakiham, Y. and Evans, P. R. (1988) J. Mol. Biol. 204, 973–994). PFK from either prokaryotic source is a tetraruer with a subunit molecular mass around 35,000 Daltons which is less than haft the mass of mammalian or S. mansoni PFK monomers. Cloning of the Haemonchus contortus PFK and crystallographic studies of PFKs from E. coli and thermophylic bacteria have provided information regarding the locations of the catalytic domains of nontrematode PFK's (Klein, R. D., Olson, E. R., Favreau, M. A., Winterrowd, C. A., Hatzenbuhler, N. T., Shea, M. H., Nulf, S. C. and Geory, T. G. (1991) Mol. Biochem. Parasitol. 48, 17–26; Evans, P. R. and Hudson, P. J. (1979) Nature 279, 500–504). The nucleic acid sequence of PFK from trematodes of the genus Schistosoma and of the related genus Fasciola has not been isolated or described, until the invention described herein.

SUMMARY OF THE INVENTION

The invention provides isolated polynucleotides comprising nucleic acid sequences at least 12 bases long and having at least 95% nucleic acid sequence homology to a corresponding nucleic acid sequence encoding Schistosoma phosphofructokinase. "Schistosoma mansoni PFK" is referred to herein as "Sm-PFK". The invention includes isolated polynucleotides having nucleic acid sequences from genera related to Schistosoma, such as Fasciola. In other embodiments the invention provides for isolated polynucleotides having nucleic acid sequences of Schistosoma mansoni PFK as described in SEQUENCE ID NO:1, nucleic acid sequences complementary to SEQUENCE ID NO: 1, and fragments at least 12 bases in length from either the nucleic acid sequence described in SEQUENCE ID NO: 1 or nucleic acid sequences complementary to the nucleic acid sequence described in SEQUENCE ID NO: 1 and which will selectively hybridize to Schistosoma nucleic acids encoding phosphofructokinase.

Another embodiment of the invention provides for PFK as an isolated protein encoded by the polynucleotides of the invention. The invention provides for Schistosoma PFK as an isolated protein with an amino acid sequence described in SEQUENCE ID NO: 2. The invention also provides for an isolated polynucleotide sequence encoding the amino acid sequence described in SEQUENCE ID NO: 2.

The invention includes vectors and cells for expressing the isolated polynucleotides of the invention when the isolated polynucleotides are operably linked to an expression vector appropriate for expression in the cell used.

The isolated polynucleotides the invention can be used as probes in detection assays for trematodes, in particular Schistosoma; and as treatments for trematodes, in particular antisense treatments for Schistosomiasis.

The isolated proteins of the invention can be used to generate antibodies for detection assays of trematodes, in particular Schistosoma.

BRIEF DESCRIPTION OF THE DRAWING

FIG. 1 Describes an immunoblot of extracts from Spodoptera frugiperda (Sf9) insect cells. Antiserum against purified PFK from Fasciola hepatica diluted 1000 times was used. Lane R contains insect cell extract of the recombinant enzyme. Lane C contains extract of insect cells that were transfected with baculovirus that had the β-galactosidase gene but no phosphofructokinase polynucleotide. Lane M contains male schistosome extracts. Lane M/F contains extracts from a mixture of male and female parasites.

DESCRIPTION OF SPECIFIC EMBODIMENTS

Novel compositions comprising isolated polynucleotides and oligonucleotides having nucleic acid sequences of trematode PFK are provided by the invention. Isolated proteins encoded by trematode PFK polynucleotides are also provided by the invention.

Exemplary nucleic acid and amino acid sequences are set forth in SEQUENCE ID Nos. 1 and 2, respectively. Broader aspects of the invention include isolated polynucleotides and oligoncleotides having nucleic acid sequences homologous to SEQUENCE ID NO: 1 or encoding SEQUENCE ID NO: 2; and isolated proteins having amino acid sequences homologous to SEQUENCE ID NO: 2.

Broad aspects of the invention are achieved by either chemically synthesizing polynucleotides or oligonucleotides encoding Sm-PFK, in whole or in part, having at least 95% nucleic acid sequence homology to a Schistosoma nucleic acid sequence encoding phosphofructokinase; or by isolating polynucleotides encoding a naturally occurring PFK and having at least 95% nucleic acid sequence homology to a nucleic acid sequence encoding phosphofructokinase from Schistosoma. For instance, techniques for synthesizing polynucleotides and oligonucleotides are well known in the art and changes can be made to the sequence of SEQUENCE ID NO: 1 that allow for deviation from that sequence while permitting at least a 95% nucleic acid sequence homology to be maintained with the sequence described in SEQUENCE ID NO:1. Such sequences share less homology with human, E. coil or H. contortus PFK nucleic acid sequences than with trematode PFK nucleic acid sequences.

Alternatively, in another embodiment of the invention polynucleotides encoding naturally occurring PFK with at least 95% nucleic acid sequence homology to a Sm-PFK nucleic acid sequence are isolated using isolated polynucleotides or oligonucleotides having nucleic acid sequences derived from SEQUENCE ID NO: 1. Hybridization and wash conditions are known in the art, and discussed herein, that can be used to selectively hybridize probe nucleic acids generated from the sequence described in SEQUENCE ID NO: 1 to nucleic acids with at least 95% nucleic acid sequence homology to Sm-PFK nucleic acid sequence.

In the isolated protein aspects of the invention, isolated proteins of PFK have amino acid sequences that correspond to nucleic acid sequences encoding a PFK having at least 95% nucleic acid sequence homology to a nucleic acid sequence encoding phosphofructokinase from Schistosoma. The isolated proteins of the invention can be expressed using the polynucleotides of the invention operably linked to an appropriate control sequence in an expression vector suitable for expression in either a mammalian, insect, yeast, or bacterial cell.

Definition of terms

A number of terms used in the art of genetic engineering and protein chemistry are used herein with the following defined meanings.

The term "isolated polynucleotide" referred to herein means a polynucleotide of genomic, cDNA, or synthetic origin or some combination there of, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence.

The term "isolated protein" referred to herein means a protein of cDNA, recombinant RNA, or synthetic origin or some combination thereof, which by virtue of its origin the "isolated protein" (1) is not associated with proteins found in nature, (2) is free of other trematode proteins, (3) is expressed by a nontrematode cell or (4) does not occur in nature. Preferably an isolated protein possesses a phosphofructokinase activity of at least 900 to 950 milliunits per mg of protein, wherein the phosphofructokinase activity is determined by the method of Choate, G. L., Lan, L. and Mansour, T. E. (1985). J. Biol. Chem. 260, 4815–4822.

The term "naturally occurring nucleic acid sequence" referred to herein means a nucleic acid sequence that encodes a phosphofructokinase enzyme found in nature. For example, phosphofructokinase from the genera Schistosoma or Fasciola.

The term "operably linked" referred to herein refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

The term "control sequence" referred to herein refers to polynucleotide sequences which are necessary to effect the expression of coding sequences to which they are ligated. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is necessary for expression, and can also include additional components whose presence is advantageous, for example, leader sequences and fusion partner sequences.

The term "oligonucleotide" referred to herein includes naturally occurring, and modified nucleotides linked together by naturally occurring, and non-naturally occurring oligonucleotide linkages. Oligonucleotides are a polynucleotide subset with 200 bases or fewer in length. Preferably oligonucleotides are 10 to 60 bases in length and most preferably 12, 13, 14, 15, 16, 17, 18, 19, or 20 to 40 bases in length. Oligonucleotides are usually single stranded, e.g. for probes; although oligonucleotides may be double stranded, e.g. for use in the construction of a gene mutant. Oligonucleotides of the invention can be either sense or antisense oligonucleotides. The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phoshoraniladate, phosphoroamidate, and the like. An oligonucleotide can include a label for detection, if desired.

The term "sequence homology" referred to herein describes the proportion of base matches between two nucleic acid sequences or the proportion amino acid matches between two amino acid sequences. When sequence homology is expressed as a percentage, e.g., 50%, the percentage denotes the proportion of matches over the length of sequence from Schistosoma PFK that is compared to some other sequence. Gaps (in either of the two sequences) are permitted to maximize matching; gap lengths of 15 bases or less are usually used, 6 bases or less are preferred with 2 bases or less more preferred. When using oligonucleotides as probes or treatments the sequence homology between the target nucleic acid and the oligonucleotide sequence is generally not less than 17 target base matches out of 20 possible oligonucleotide base pair matches (85%); preferably not less than 9 matches out of 10 possible base pair matches (90%), and most preferably not less than 19 matches out of 20 possible base pair matches (95%).

The term "selectively hybridize" referred to herein means to detectably and specifically bind. Polynucleotides, oligonucleotides and fragments of the invention selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, and fragments of the invention and a nucleic acid sequence of interest will be at least 95%.

Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred.

Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in *Atlas of Protein Sequence and Structure*, 1972, volume 5, National Biomedical Research Foundation, pp. 101–110, and Supplement 2 to this volume, pp. 1–10. The two sequences or parts thereof are more preferably homologous if their amino acids are greater than or equal to 50% identical when optimally aligned using the ALIGN program.

The term "polynucleotide" as referred to herein means a polymeric form of nucleotides of at least 10 bases in length, either fibonucleotides or deoxynucleotides or a modified form of either type of nucleotide. The term includes single and double stranded forms of DNA.

The term "fragments" as referred to herein means a portion of a polynucleotide, usually at least 12 bases or base pairs in length. Preferably fragments are at least 18 bases or base pairs in length. Fragments are derived by a cleavage reaction, preferably a hydrolysis reaction.

Detection Of Trematode Nucleic Acid Using Trematode PFK Polynucleotides

The isolated polynucleotides of the invention can be used as probes to detect the presence of Schistosoma and related organisms in a sample. The sample is typically from blood or water. (Sambrook, J., Fritsch, E. F., and Maniatis, T., *Molecular Cloning*, second edition (1989) (referred to herein as "Sambrook et al.") The isolated polynucleotides can be used to detect Schistosoma, Fasciola, Clonorchis, or Heterophye. Isolated polynucleotides with nucleic acid sequences encoding PFK (e.g. SEQ ID NO:1) can be used as probes to detect the presence of target nucleic acid sequences with sequence homology. Polynucleotide probes are prepared and labelled by methods known in the art, e.g., Sambrook et al, especially chapter 10, the text of sections on preparing and labelling nucleic acids is herein incorporated by reference. For example, the polymerase chain reaction can be used m amplify the DNA and a biotin-avidin label system can be used to label and detect the target polynucleotide. Polynucleotide probes are hybridized with target nucleic acids at appropriate hybridization temperatures (e.g. see Sambrook et al; the text of Chapter 9 is herein incorporated by reference); and washed at low and high wash stringencies, depending on the detection assay.

At low stringency wash conditions, probes based on polynucleotides can potentially bind to PFK nucleic acids unrelated to trematode parasites, such as human, bacteria, or nematode PFK nucleic acids. Using a convenient low stringency condition (e.g., 2× SCC, 0.1% SDS, room temperature twice, 30 minutes each; then 2× SCC, 0.1% SDS, 50° C. once, 30 minutes; then 2× SCC, room temperature twice, 10 minutes each) homologous sequences can be identified that contain at most about 25–30% base pair mismatches. More preferably, homologous nucleic acid strands contain 15–25% base pair mismatches, even more preferably 5–15% base pair mismatches. These degrees of homology can be selected by using more stringent wash conditions for identification of clones from gene libraries (or other sources of genetic material), as is well known in the art.

When isolated polynucleotides are used as probes at low stringency it is desirable to reduce the number of false positives in the detection assay. Cells unrelated to the trematode parasites being detected (e.g. host cells or water born bacteria) can be removed by techniques known in the art (e.g. differential centrifugation) from the sample being tested. Polynucleotides with nucleic acid sequences shorter than the 3047 base pair full length clone, are desirable for use as low stringency probes because shorter nucleic acid sequences will contain less homology to generally conserved regions of the PFK polynucleotide (e.g. the fructose-6-phosphate and ATP binding domains of PFK). Shorter polynucleotide probes may contain either the fructose-6-phosphate or the ATP binding domains, so long as the nucleic acid sequence homology to the human PFK nucleic acid sequence remains less than 80% (Sharma, P. M., Reddy, G. R., Vora, S., Babior, B. M. and McLachlan, A. (1989) Gene 77, 177–183) or the nucleic acid sequence homology to the nematode PFK nucleic acid sequence remains less than 80% (Klein, R. D., Olson, E. R., Favreau, M. A., Winterrowd, C. A., Hatzenbuhler, N. T., Shea, M. H., Nulf, S. C. and Geory, T. G. (1991) Mol. Biochem. Parasitol. 48, 17–26). To increase the specificity of the probes for organisms of the genus Schistosoma and Fasciola, and decrease the likelihood of cross hybridization with bacteria or human PFK nucleic acids, probes are selected from regions of the Sm-PFK sequence that do not contain amino acids that are involved in the fructose-6phosphate or ATP sites as determined by crystallographic data for *E. coli* (in Sm-PFK the phosphofructokinase binding site comprises amino acids $Ser_{166}$, $Asp_{168}$, $Asp_{170}$, $Arg_{203}$, $Met_{210}$, $Gly_{211}$, $Arg_{212}$, $Glu_{266}$, $Arg_{294}$, $His_{300}$, $Arg_{303}$, $Thr_{537}$, $Ser_{539}$, $Asn_{541}$, $Arg_{575}$, $Met_{582}$, $Gly_{583}$, $Gly_{584}$, $Asp_{638}$, $Arg_{664}$, $His_{670}$, and $Gln_{673}$; and the ATP binding site comprises amino acids $Gly_{27}$, $Tyr_{57}$, $Arg_{90}$, $Cys_{91}$, $Arg_{95}$, $Asp_{121}$, $Gly_{122}$, $Ser_{123}$, $Thr_{125}$, $Gly_{126}$, $Ala_{418}$, $Phe_{448}$, $Arg_{479}$, $Asp_{480}$, $Gly_{483}$, $Phe_{508}$, $Glu_{509}$, $Ala_{510}$, $Glu_{512}$, and $Cys_{513}$) (See *E. Coli* data of Evans, P. R. and Hudson, P. J. (1979) Nature 279, 500–504).

Preferably polynucleotides are used as probes under high stringency wash conditions and with corresponding hybridization conditions, as known in the art. Isolated polynucleotides can be used to make probes that are 50 base pairs to the full length of pSm-PFK (3047 base pairs). Preferably probes are made from isolated polynucleotides 100–400 nucleotides in length. Probes are preferably selected from the regions of the Sm-PFK nucleic acid sequence that are not conserved between human PFK or *E. coli* PFK. To provide probes with greater specificity to PFK from organisms of the genus Schistosoma than to PFK of human or *E. coli* origin, probes are selected from a region of the Sm-PFK nucleic acid sequence that does not encode amino acids that are involved in the fructose-6phosphate or ATP binding sites as determined by crystallographic data for *E. coli* (In Sm-PFK the phosphofructokinase binding site comprises amino acids $Ser_{166}$, $Asp_{168}$, $Asp_{170}$, $Arg_{203}$, $Met_{210}$, $Gly_{211}$, $Arg_{212}$, $Glu_{266}$, $Arg_{294}$, $His_{300}$, $Arg_{303}$, $Thr_{537}$, $Ser_{539}$, $Asn_{541}$, $Arg_{575}$, $Met_{582}$, $Gly_{583}$, $Gly_{584}$, $Asp_{638}$, $Arg_{664}$, $His_{670}$, and $Gln_{673}$; and the ATP binding site comprises amino acids $Gly_{27}$, $Tyr_{57}$, $Arg_{90}$, $Cys_{91}$, $Arg_{95}$, $Asp_{121}$, $Gly_{122}$, $Ser_{123}$, $Thr_{125}$, $Gly_{126}$, $Ala_{418}$, $Phe_{448}$, $Arg_{479}$, $Asp_{480}$, $Gly_{483}$, $Phe_{508}$, $Glu_{509}$, $Ala_{510}$, $Glu_{512}$, and $Cys_{513}$) (See *E-Coli* data of Evans, P. R. and Hudson, P. J. (1979) Nature 279, 500–504).

Alternatively, oligonucleotides can be employed as probes. Techniques for using oligonucleotides as probes to detect the same or related nucleic acid sequences is well known in the art, see for example Sambrook et al, especially Chapter 11, the text of which is herein Incorporated by reference. Probes can be made from oligonucleotides that are 10 to 200 bases in length. Preferably probes are made from oligonucleotides 10 to 60 nucleotides in length and most preferably 12 to 40 bases in length. Probes are preferably selected from the regions of the Sm-PFK nucleic acid sequence that are not conserved between human PFK or *E. coli* PFK. To provide probes with greater specificity to PFK from organisms of the genus Schistosoma than to PFK of human or *E. coli*, probes are selected from regions of the Sm-PFK sequence that do not contain amino acids that are involved in the fructose-6-phosphate or ATP sites as determined by crystallographic data for *E. coli* (In Sm-PFK the phosphofructokinase binding site comprises amino acids $Ser_{166}$, $Asp_{168}$, $Asp_{170}$, $Arg_{203}$, $Met_{210}$, $Gly_{211}$, $Arg_{212}$, $Glu_{266}$, $Arg_{294}$, $His_{300}$, $Arg_{303}$, $Thr_{537}$, $Ser_{539}$, $Asn_{54}$, $Arg_{575}$, $Met_{582}$, $Gly_{583}$, $Gly_{584}$, $Asp_{638}$, $Arg_{664}$, $His_{670}$, and $Gln_{673}$; and the ATP binding site comprises amino acids $Gly_{27}$, $Tyr_{57}$, $Arg_{90}$, $Cys_{91}$, $Arg_{95}$, $Asp_{121}$, $Gly_{122}$, $Ser_{123}$, $Thr_{125}$, $Gly_{126}$, $Ala_{418}$, $Phe_{448}$, $Arg_{479}$, $Asp_{480}$, $Gly_{483}$, $Phe_{508}$, $Glu_{512}$, $Ala_{510}$, $Glu_{512}$, and $Cys_{513}$) (See *E. Coli* data of Evans, P. R. and Hudson, P. J. (1979) Nature 279, 500–504).

One method for amplification of target nucleic acids, for later analysis by hybridization assays, is known as the polymerase chain reaction ("PCR") or PCR technique. The PCR technique can be applied to detect sequences of the invention in suspected samples using oligonucleotide primers spaced apart from each other and based on the genetic sequence set forth herein. The primers are complementary to opposite strands of a double stranded DNA molecule and are typically separated by from about 50 to 450 nucleotides or more (usually not more than 2000 nucleotides). This method entails preparing the specific oligonucleotide primers followed by repeated cycles of target DNA denaturation, primer binding, and extension with a DNA polymerase to obtain DNA fragments of the expected length based on the primer spacing. Extension products generated from one primer serve as additional target sequences for the other primer. The degree of amplification of a target sequence is controlled by the number of cycles that are performed and is theoretically calculated by the simple formula 2n where n is the number of cycles. Given that the average efficiency per cycle ranges from about 65% to 85%, 25 cycles produce from 0.3 to 4.8 million copies of the target sequence. The PCR method is described in a number of publications, including 65 % to 85 %, 25 cycles produce from 0.3 to 4.8 million copies of the target sequence. The PCR method is described in a number of publications, including Saiki et al., Science (1985) 230:1350–1354; Saiki et al., Nature (1986) 324:163–166; and Scharf et al., Science (1986) 233:1076–1078. Also see U.S. Pat. Nos. 4,683,194; 4,683, 195; and 4,683,202, the text of each patent is herein incorporated by reference.

The invention includes a specific diagnostic method for determination of trematode nucleic acid, based on selective amplification of trematode PFK DNA fragments. The method is particularly well suited to Schistosoma nucleic acids encoding PFK. This method employs a pair of single-strand primers derived from non-homologous regions of opposite strands of a Schistosoma PFK DNA duplex fragment having a sequence as described in SEQ ID NO: 1. These "primer fragments" represent one aspect of the invention. The method follows the process for amplifying selected nucleic acid sequences as disclosed in U.S. Pat. No. 4,683, 202, as discussed herein.

Protein Expression

Vectors suitable for replication in mammalian cells are known in the art, and can include viral replicons, or sequences that ensure integration of the sequence encoding PFK into the host genome. Suitable vectors can include, for example, those derived from simian virus SV40, retroviruses, bovine papilloma virus, vaccinia virus, and adenovirus.

A suitable vector, for example, is one derived from vaccinia viruses. In this case, the heterologous DNA is inserted into the vaccinia genome. Techniques for the insertion of foreign DNA into the vaccinia virus genome are known in the art, and utilize, for example, homologous recombination. The insertion of the heterologous DNA is generally into a gene which is non-essential in nature, for example, the thymidine kinase gene (tk), which also provides a selectable marker. Plasmid shuttle vectors that greatly facilitate the construction of recombinant viruses have been described (see, for example, Mackett et al. (1984), Chakrabarti et al. (1985); Moss (1987)). Expression of the heterologous polypeptide then occurs in cells or individuals which are immunized with the live recombinant vaccinia virus.

Such suitable mammalian expression vectors usually contain one or more eukaryotic transcription units that are capable of facilitating expression in mammalian cells. The transcription unit is comprised of at least a promoter element to mediate transcription of foreign DNA sequences. Suitable promoters for mammalian cells are known in the an and include viral promoters such as that from simian virus 40 (SV40), cytomegalovirus (CMV), Rous sarcoma virus (RSV), adenovirus (ADV), and bovine papilloma virus (BPV).

The optional presence of an enhancer element (enhancer), combined with the promoter elements described herein, will typically increase expression levels. An enhancer is any regulatory DNA sequence that can stimulate transcription up to 1000-fold when linked to endogenous or heterologous promoters, with synthesis beginning at the normal mRNA start site. Enhancers are also active when they are placed upstream or downstream from the transcription initiation site, in either normal or flipped orientation, or at a distance of more than 1000 nucleotides from the promoter (Maniatis et al. (1987) Science 236:1237; Alberts et al. (1989) Molecular Biology of the Ceil, 2end ed. ). Enhancer elements derived from viruses can be particularly useful, because they typically have a broader host range. Examples useful in mammalian cells include the SV40 early gene enhancer (Dijkema et al (1985) EMBO J. 4:761) and the enhancer/promoters derived from the long terminal repeat (LTR) of the Rous Sarcoma Virus (Gorman et al. (1982b) Proc. Natl. Atari. Sci. 79:6777) and from human cytomegalovirus (Boshart et al. (1985) Cell 41:521). Additionally, some enhancers are regulatable and become active only in the presence of an inducer, such as a hormone or metal ion (Sassone-Corsi and Borelli (1986) Trends Genet. 2:215; Manlatis et al. (1987) Science 236:1237).

In addition, the transcription unit can also be comprised of a termination sequence and poly(A) addition sequences which are operably linked to the PFK coding sequence. The transcription unit can also be comprised of an enhancer sequence which increases the expression of PFK.

Sequences that cause amplification of the gene may also be desirable, as are sequences which encode selectable markers. Selectable markers for mammalian cells are known in the art, and include for example, thymidine kinase, dihydrofolate reductase (together with methotraxate as a DHFR amplifier), aminoglycoside phosphotransferase, hygromycin B phosphotransferase, asparagine synthetase, adenosine deaminase, metallothionien, and antibiotic resistant genes such as neomycin.

The vector that encodes PFK can be used for transformation of a suitable mammalian host cell. Transformation can be by any known method for introducing polynucleotides into a host cell, including, for example packaging the polynucleotide in a virus and transducing a host cell with the virus or by transfection procedures known in the art, as exemplified by U.S. Pat. Nos. 4,399,216; 4,912,040; 4,740, 461; 4,959,455 (these patents are incorporated herein by reference). The transformation procedure used depends upon the host to be transformed. Methods for introduction of heterologous polynucleotides into mammalian cells are known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines.

In the case of expression in insect cells, generally the components of the expression system include a transfer vector, usually a bacterial plasmid, which contains both a fragment of the baculovirus genome, and a convenient restriction site for insertion of the heterologous gene or genes to be expressed; a wild type baculovims with a sequence homologous to the baculovims-specific fragment in the transfer vector (this allows for the homologous recombination of the heterologous gene in to the baculovirus genome); and appropriate insect host cells and growth media.

One of the most commonly used transfer vector for introducing foreign genes into AcNPV is pAc373. Many other vectors, known to those of skill in the art, have also been designed. These include, for example, pVL985 (which alters the polyhedrin start codon from ATG to ATT, and which introduces a BamHI cloning site 32 base pairs downstream from the ATT; see Luckow and Summers, Virology (1989) 17:31.

The plasmid usually also contains the polyhedrin polyadenylation signal (Miller et al. (1988) Ann. Rev. Microbiol., 42:177) and a procaryotic ampicillin-resistance (amp) gene and origin of replication for selection and propagation in E. coli.

Baculovirus transfer vectors usually contain a baculovirus promoter. A baculovirus promoter is any DNA sequence capable of binding a baculovirus RNA polymerase and initiating the downstream (5' to 3') transcription of a coding sequence (e.g. structural gene) into mRNA. A promoter will have a transcription initiation region which is usually placed proximal to the 5' end of the coding sequence. This transcription initiation region typically includes an RNA polymerase binding site and a transcription initiation site. A baculovirus transfer vector can also have a second domain called an enhancer, which, if present, is usually distal to the structural gene. Expression can be either regulated or constitutive.

Additionally, the PFK polynucleotide or a fragment thereof can be expressed in a bacterial system. Therein, a bacterial promoter is any DNA sequence capable of binding bacterial RNA polymerase and initiating the downstream (3') transcription of a coding sequence (e.g. structural gene) into mRNA. A promoter will have a transcription initiation region which is usually placed proximal to the 5' end of the coding sequence. This transcription initiation region typically includes an RNA polymerase binding site and a transcription initiation site. A bacterial promoter can also have a second domain called an operator, that can overlap an adjacent RNA polymerase binding site at which RNA synthesis begins. The operator permits negative regulated (inducible) transcription, as a gene repressor protein can bind the operator and thereby inhibit transcription of a specific gene. Constitutive expression can occur in the absence of negative regulatory elements, such as the operator. In addition, positive regulation can be achieved by a gene activator protein binding sequence, which, if present is usually proximal (5') to the RNA polymerase binding sequence. An example of a gene activator protein is the catabolite activator protein (CAP), which helps initiate transcription of the lac operon in Escherichia coli (*E. coli*) [Raibaud et al. (1984) Annu. Rev. Genet. 18:173]. Regulated expression can therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) [Chang et at. (1977) Nature 198:1056], and maltose. Additional examples include promoter sequences derived from biosynthetic enzymes such as tryptophan (trp) [Goeddel et at. (1980) Nuc. Acids Res. 8:4057; Yelverton et al. (1981) Nucl. Acids Res. 9:731; U.S. Pat. No. 4,738,921; E.P.O. Pub. Nos. 36,776 and 121,775]. The ■-lactomase (bla) promoter system [Weissmann (1981). In Interferon 3 (ed. I. Gresser)], bacteriophage lambda PL [Shimatake et al. (1981) Nature 292:128] and T5 [U.S. Pat. No. 4,689,406] promoter systems also provide useful promoter sequences.

In addition, synthetic promoters which do not occur in nature also function as bacterial promoters. For example, transcription activation sequences of one bacterial or bacteriophage promoter can be joined with the operon sequences of another bacterial or bacteriophage promoter, creating a synthetic hybrid promoter [U.S. Pat. No. 4,551, 433]. For example, the tac promoter is a hybrid trp-lac promoter comprised of both trp promoter and lac operon sequences that is regulated by the lac repressor [Amann et al. (1983) Gene 25:167; de Boer et al. (1983) Proc. Natl. Acad. Sci. 80:21]. Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system [Studier et al. (1986) J. Mol. Biol. 189:113; Tabor et al. (1985) Proc Natl. Acad. Sci. 82:1074]. In addition, a hybrid promoter can also be comprised of a bacteriophage promoter and an E. coli operator region (E.P.O. Pub. No. 267,851).

In addition to a functioning promoter sequence, an efficient ribosome binding site is also useful for the expression of the PFK gene or fragment thereof in prokaryotes. In E. coli, the ribosome binding site is called the Shine-Dalgarno (SD) sequence and includes an initiation codon (ATG) and a sequence 3–9 nucleotides in length located 3–11 nucleotides upstream of the initiation codon [Shine et al. (1975) Nature 254:34]. The SD sequence is thought to promote binding of mRNA to the ribosome by the pairing of bases between the SD sequence and the 3' and of E. coli 16S rRNA [Steitz et al. (1979). In Biological Regulation and Development: Gene Expression (ed. R. F. Goldberger)]. To express eukaryotic genes and prokaryotic genes with weak ribosome-binding site [Sambrook et al. (1989) "Expression of cloned genes in Escherichia coli". In Molecular Cloning: A Laboratory Manual].

PFK can be expressed intracellularly. A promoter sequence can be directly linked with the PFK gene or a fragment thereof, in which case the first amino acid at the N-terminus will always be a methionine, which is encoded by the ATG start codon. If desired, methionine at the N-terminus can be cleaved from the protein by in vitro incubation with cyanogen bromide or by either in vivo on in vitro incubation with a bacterial methionine N-terminal peptidase (E.P.O. Pub. No. 219,237).

Fusion proteins provide an alternative to direct expression. Typically, a DNA sequence encoding the N-terminal portion of an endogenous bacterial protein, or other stable protein, is fused to the 5'end of heterologous PFK coding sequences. Upon expression, this construct will provide a fusion of the two amino acid sequences. For example, the bacteriophage lambda cell gene can be linked at the 5' terminus of the PFK gene or fragment thereof and expressed in bacteria. The resulting fusion protein preferably retains a site for a processing enzyme (factor Xa) to cleave the bacteriophage protein from the PFK gene or fragment thereof [Nagai et al. (1984) Nature 309:8101]. Fusion proteins can also be made with sequences from the lacZ [Jia et al. (1987) Gene 60:197], trpE [Allen et al. (1987) J. Biotechnol. 5:93; Makoff et at. (1989) J. Gem Microbiol. 135:11], and Chey [E.P.O. Pub. No. 324,647] genes. The DNA sequence at the junction of the two amino acid sequences may or may not encode a cleavable site. Another example is a ubiquitin fusion protein. Such a fusion protein is made with the ubiquitin region that preferably retains a site for a processing enzyme (e.g. ubiquitin specific processing-protease) to cleave the ubiquitin from the PFK polypeptide. Through this method, mature PFK polypeptides can be isolated [Miller et al. (1989) Bio/Technology 7:698].

Alternatively, PFK polypeptides can also be secreted from the cell by creating chimeric DNA molecules that encode a fusion protein comprised of a signal peptide sequence fragment that provides for secretion of the PFK polypeptides in bacteria [U.S. Pat. No. 4,336,336]. The signal sequence fragment typically encodes a signal peptide comprised of hydrophobic amino acids which direct the secretion of the protein from the cell. The protein is either secreted into the growth media (gram-positive bacteria) or into the periplasmic spece, located between the inner and outer membrane of the cell (gram-negative bacteria). Preferably there are processing sites, which can be cleaved either in vivo or in vitro encoded between the signal peptide fragment and the PFK polypeptide.

DNA encoding suitable signal sequences can be derived from genes for secreted bacterial proteins, such as the E. coli outer membrane protein gene (ompA) [Masui et al. (1983), in: Experimental Manipulation of Gene Expression; Ghrayeb et at. (1984) EMBO J. 3:2437] and the E. coli alkaline phosphatase signal sequence (phoA) [Oka et al. (1985) Proc. Natl. Acad. Sci. 82:7212]. As an additional example, the signal sequence of the alpha-amylase gene from various Bacilus strains can be used to secrete heterologous proteins from B. subtilis [Palva et al. (1982) Proc. Natl. Acad. Sci. USA 79:5582; E.P.O. Pub. No. 244,042].

Typically, transcription termination sequences recognized by bacteria are regulatory regions located 3'to the translation stop codon, and thus together with the promoter flank the coding sequence. These sequences direct the transcription of an mRNA which can be translated into the polypeptide encoded by the DNA. Transcription termination sequences frequently include DNA sequences of about 50 nucleotides capable of forming stem loop structures that aid in terminating transcription. Examples include transcription termination sequences derived from genes with strong promoters, such as the trp gene in E. coli as well as other biosynthetic genes.

Typically, the above described components, comprising a promoter, signal sequence (if desired), coding sequence of interest, and transcription termination sequence, are put together into expression constructs. Expression constructs are often maintained in a replicon, such as an extrachromosomal element (e.g., plasmids) capable of stable maintenance in a host, such as bacteria. The replicon will have a replication system, thus allowing it to be maintained in a procaryotic host either for expression or for cloning and amplification. In addition, a replicon can be either a high or low copy number plasmid. A high copy number plasmid will generally have a copy number ranging from about 5 to about 200, and typically about 10 to about 150. A host containing a high copy number plasmid will preferably contain at least about 10, and more preferably at least about 20 plasmids. Either a high or low copy number vector can be selected, depending upon the effect of the vector and the PFK polypeptide on the host.

Alternatively, the expression constructs can be integrated into the bacterial genome with an integrating vector. Integrating vectors typically contain at least one sequence homologous to the bacterial chromosome that allows the vector to integrate. Integrations appear to result from recombinations between homologous DNA in the vector and the bactedrial chromosome. For example, integrating vectors constructed with DNA from various Bacillus strains integrate into the Bacillus chromosome (E.P.O. Pub. No. 127, 328). Integrating vectors can also be comprised of bacteriophage or transposon sequences.

Typically, extrachromosomal and integrating expression constructs can contain selectable markers to allow for the selection of bacterial strains that have been transformed.

Selectable markers can be expressed in the bacterial host and can include genes which render bacteria resistant to drugs such as ampicillin, chloramphenicol, erythromycin, kanamycin (neomycin), and tetracycline [Davies et al. (1978) Annu. Rev. Microbiol. 32:469]. Selectable markers can also include biosynthetic genes, such as those in the histidine, tryptophan, and leucine biosynthetic pathways.

Alternatively, some of the above described components can be put together in transformation vectors. Transformation vectors are typically comprised of a selectable marker that is either maintained in a replicon or developed into an integrating vector, as described above.

Expression and transformation vectors, either extra-chromosomal replicons or integrating vectors, have been developed for transformation into many bacteria. For example, expression vectors have been developed for, inter alia, the following bacteria: *Bacillus subtilis* [Palva et al. (1.982) Proc. Natl. Acad. Sci. USA 79:5582; E.P.O. Pub. Nos. 36,259 and 63,953; P.C.T. WO 84/04541], *Escherichia coli* [Shimatake et al. (1981) Nature 292:128; Amann et al. (1985) Gene 40:183; Studier et al. (1986) J. Mol. Biol. 189:113; E.P.O. Pub. Nos. 36,776, 136,829 and 136,907; U.K. Patent Application Serial No. 8418273], *Streptococcus cremoris* [Powell et al. (1988) Appl. Environ. Microbiol. 54:655] *Streptococcus lividans* [Powell et al. (1988) Appl. Environ. Microbiol. 54:655], *Streptomyces lividans* [U.S. Pat. No. 4,745,056].

Methods of introducing exogenous DNA into bacterial hosts are well-known in the art, and typically include either the transformation of bacteria treated with $CaCl_2$ or other agents, such as divalent cations and DMSO. DNA can also be introduced into bacterial cells by electropotation. Transformation procedures usually vary with the bacterial species to be transformed. See e.g., [Masson et al. (1989) FEMS Microbiol. Lett. 60:273; Palva et al. (1982) Proc. Natl. Acad. Sci. USA 79:5582; E.P.O. Pub. Nos. 36,259 and 63,953; P.C.T. WO 84/04541, Bacillus], [Miller et al. (1988) Proc. Natl. Acad. Sci. 85:856; Wang et al. (1990) J. Bacteriol. 172:949, Campylobacter], [Cohen et al. (1973) Proc. Natl. Acad. Sci. 69:2110; Dower et al. (1988) Nucleic Acids Res. 16:6127; Kushner (1978) An improved method for transformation of *Escherichia coli* with ColEl-derived plasmids. In Genetic Engineering: Proceedings of the International Symposium on Genetic Engineering (eds. H. W. Boyer and S. Nicosia); Mandel et al. (1970) J. Mol. Biol. 53:159; Taketo (1988) Biochim. Biophys. Acta 949:318; Escherichia], [Chassy et al. (1987) FEMS Microbiol. Lett. 44:173 Lactobacillus]; [Fiedler et al. (1988) Anal. Biochem 170:38, Pseudomonas]; [Augustin et al. (1990) FEMS Microbiol. Lett. 66:203, Staphylococcus], [Barany et al. (1980)J. Bacteriol. 144:698; Harlander (1987) "Transformation of *Streptococcus lactis* by electroporation", in: Streptococcal Genetics (ed. J. Ferretti and R. Curtiss III); Perry et al. (1981) Infec. Immun. 32:1295; Powell et al. (1988) Appl. Environ. Microbiol. 54:655; Somkuti et al. (1987) Proc. 4th Evr. Cong. Biotechnology 1:412, Streptococcus].

Trematode PFK polynucleotides can be introduced into either mutant or nonmutant bacteria. For instance, trematode PFK polynucleotides can be introduced into strain DF1020 (Daldal J. Mol. Biol. 168:285 (1983) which lacks PFK activity. When trematode PFK polynucleotides are expressed in the bacteria, the mutant bacteria will grow. If the culture is treated with a putative inhibitor of Sm-PFK, or some other trematode PFK, the effectiveness of the inhibitor can be measured.

As discussed herein, minor variations in the amino acid sequence of Sm-PFK protein are contemplated as being encompassed by the term trematode PFK, providing that the minor variations in the amino acid sequence maintain at least 95% homology to a nucleic acid sequence encoding Sm-PFK; in particular, conservative amino acid replacements are contemplated. Conservative replacements are those that take place within a family of amino acids that are related in their side chains. Genetically encoded amino acids are generally divided into four families: (1) acidic=aspartate, glummate; (2)basic=leucine, arginine, histidine; (3) nonpolar=alanine, valine, leucine, isoleucine, proline, phenylalanine, methionine, tryptophan; and (4)uncharged polar= glycine, asparagine, glutamine, cystine, serine, threonine, tyrosine. Phenylalanine, tryptophan, and tyrosine are sometimes classified jointly as aromatic amino acids. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding properties of the resulting molecule, especially if the replacement does not involve an amino acid at a binding site involved in the interaction of Sm-PFK protein or its derivatives with ATP or fructose-6-phosphate. Whether an amino acid change results in a functional peptide can readily be determined by assaying the specific activity of the polypeptide derivative. An activity assay is described in detail herein.

Antisense Treatments

The antisense oligonucleotides of the invention can be synthesized by any of the known chemical oligonucleotide synthesis methods. Such methods are generally described, for example, in Winnacker, *From Genes to Clones: Introduction to Gene Technology*. VCH Verlagsgesellschaft mbH (H., Ibelgaufts trans. 1987).

Any of the known methods of oligonucleotide synthesis can be utilized in preparing the instant antisense oligonucleotides.

The antisense oligonucleotides are most advantageously prepared by utilizing any of the commercially available, automated nucleic acid synthesizers. The device utilized to prepare the oligonucleotides described herein, the Applied Biosystems 380B DNA Synthesizer, utilizes β-cyanoethyl phosphoramidite chemistry.

Antisense oligonucleotides hybridizable with any portion of the mRNA transcript can be prepared by the oligonucleotide synthesis methods known to those skilled in the art.

While any length oligonucleotide can be utilized in the practice of the invention, sequences shorter than 12 bases may be less specific in hybridizing to the target PFK mRNA, and may be more easily destroyed by enzymatic digestion. Hence, oligonucleotides having 12 or more nucleotides are preferred. Sequences longer than 18 to 21 nucleotides may be somewhat less effective in inhibiting PFK translation because of decreased uptake by the target cell. Thus, oligomers of 12–21 nucleotides are most preferred in the practice of the present invention, particularly oligomers of 12–18 nucleotides.

Oligonucleotides complementary to and hybfidizable with any portion of the PFK mRNA transcript are, in principle, effective for inhibiting translation of the transcript, and capable of inducing the effects herein described. Translation is most effectively inhibited by blocking the mRNA at a site at or near the initiation codon. Thus, oligonucleotides complementary to the 5'-terminal region of the PFK mRNA transcript are preferred. Secondary or tertiary structure which might interfere with hybridization is minimal in this region. Moreover, sequences that are too distant in the 3' direction from the initiation site can be less effective in hybridizing the mRNA transcripts because of a "read-through" phenomenon whereby the ribosome is postulated to unravel the antisense/sense duplex to permit translation of the message. (see, e.g. Shakin, J. Biochemistry 261, 16018 (1986)).

The antisense oligonucleotide is preferably directed to a site at or near the ATG initiation codon for protein synthesis. Oligonucleotides complementary to a portion of the PFK mRNA including the initiation codon are preferred. While antisense oligomers complementary to the 5'-terminal region of the PFK transcript are preferred, particularly the region including the initiation codon, it should be appreciated that useful antisense oligomers are not limited to those complementary to the sequences found in the translated portion of the mRNA transcript, but also includes oligomers complementary to nucleotide sequences contained in, or extending into, the 5' and 3'-untranslated regions.

EXAMPLES

Example 1

Construction and Screening of A λ ZAP cDNA Library From *Schistosoma mansoni*.

*Schistosoma mansoni* was used as a source of RNA for the cDNA library. The life cycle of *Schistosoma mansoni* was maintained using a Puerto Rican strain of *Biomphalaria glabrata* snails and Swiss-Webster mice. Adult worms were obtained by portal perfusion of infected mice as described by Duvall and DeWitt (Duvall, R. H. and DeWitt, W. B. (1967) Am. J. Trop. Med. Hyg. 16, 483–486). Batches of collected parasites were frozen and stored in liquid nitrogen until used. RNA was prepared from frozen parasites according to the methods known in the art (e.g. see Sambrook et al, especially chapter 7, the text of which is herein incorporated by reference).

A λ phage cDNA library was constructed in λ ZAP (Stratagene, LaJolla, Calif.) according to the procedure of Gubler and Hoffman (Gulber, U. and Hoffman, B. J. (1983). Gene 25,263–269). The library was screened using a 1.2-kb EcoRV-EcoRI fragment of the human muscle PFK cDNA clone "pc HPFKM1" (gift of Dr. McLachlan), (Sharma, P. M., Reddy, G. R., Vora, S., Babior, B. M. and McLachlan, A. (1989) Gene 77, 177–183). The EcoRV-EcoRI fragment was radiolabelled by random priming (Sambrook, J, Fritsch, E. F. and Maniatis, T. (1989) 2nd edition. Cold Spring Harbor Laboratory Press, Cold Spring Harbor, N.Y.) and used as a probe ($1\times10^6$ cpm ml$^{-1}$). Hybridization was performed overnight in DNA hybridization buffer containing 6× SSC/5× Denhardt's solution/20% formamide/10% dextran sulfate/50 mM sodium phosphate, pH 6.8/100 μg ml$^{-1}$ salmon sperm DNA. Filters were washed twice with 2× SSC containing 0.1% SDS at room temperature for 20 min, then with 1× SSC/0.1% SDS at 55° C. for 20 min. Blots were exposed overnight to Kodak XAR-5 film at −70° C. The pBluescfipt SK$^+$ plasmid containing the cDNA inserts that remained positive after 3 rounds of plaque purification were released from the λ ZAP vector by in vivo excision with the helper phage M13 K07, according to the manufacturer's instructions (Stratagene).

Example 2

DNA Sequencing of Isolated PFK Clone, pSm-PFK

From approximately $7\times10^5$ bacteriophage screened, 12 positive clones were initially identified. Of these clones, 5 remained positive after a third round of cloning and screening. Two of these clones had inserts of approximately 3.1 kb while the other three had inserts of approximately 2.9 kb. Results based on sequence analysis and restriction enzyme mapping of the 3.1-kb clones indicated that they are the same. The shorter clones, which were missing 200 bp from the 5' end, share the same 3' nucleotide sequence when compared to the 3.1-kb clones. The plasmid containing the longest cDNA insert (3047 bp) was designated pSm-PFK and sequenced.

Both strands of the cDNA inserts were sequenced by the Sanger dideoxynucleotide procedure with Sequenase (USB, Columbus, Ohio) using synthesized oligonucleotides as primers. The sequence was confirmed by sequencing the antisense strand of another independent cDNA insert obtained from the same library. Oligo primers were prepared on a DNA Synthesizer (Model 391 PCR-MATE EP™, Applied Biosystems), deprotected and cleaved according to manufacturer's instructions, and purified by standard procedures (Sambrook, J, Fritsch, E. F. and Maniatis, T. (1989) 2nd edition. Cold Spring Harbor Laboratory Press, Cold Spring Harbor, N.Y.).

Analysis of nucleotide sequences was performed using a VAX computer and the Genetics Computer Group Sequence Analysis Software Package (Version 7.0) from the University of Wisconsin (Devereux, J., Haeberii, P. and Smithies, O. (1984) Nucleic Acids Res. 12, 387–394). DNA sequences of other PFKs were obtained from GenBank data base (release 69.0).

The *Schistosoma mansoni* PFK nucleic acid sequence was deposited in GenBank (Genbank accession number L31531). The nucleic acid sequence of *Schistosoma mansoni* PFK includes 146 nucleotides of 5'-untranslated region, 2346 nucleotides of the open reading frame, and 554 nucleotides of 3'-untranslated region which is highly A/T rich (75%) (SEQUENCE ID NO: 1). The open reading frame codes for a polypeptide of 781 amino acids (SEQUENCE ID NO: 2) with a calculated molecular weight of 86,000, which is similar in number of amino acids and molecular weight to PFKs from human muscle (Sharma, P. M., Reddy, G. R., Vora, S., Babior, B. M. and McLachlan, A. (1989) Gene 77, 177–183) and the nematode parasite *Haemonchus contortus* (Klein, R. D., Olson, E. R., Favreau, M. A., Winterrowd, C. A., Hatzenbuhler, N. T., Shea, M. H., Nulf, S. C. and Geory, T. G. (1991) Mol. Biochem. Parasitol. 48, 17–26). For comparison, the alignment of the deduced amino acid sequence of Sm-PFK with that of human muscle PFK was carried out. Sm-PFK amino acid sequence has a match with the human muscle PFK amino acid sequence of 58% when gaps in the amino acid sequence are provided to maximize matching and a match of 73% when conserved amino acid substitutions are considered. (The 73% figure is also produced by providing gaps in the amino acid sequence). The Sm-PFK amino acid sequence has a match with the nematode *H. contortus* amino acid sequence of 54% when gaps in the amino acid sequence are provided to maximize matching and a match of 74% when conserved amino acids substitutions are considered (the nematode *H. contortus* amino acid sequence is from Klein, R. D., Olson, E. R., Favreau, M. A., Winterrowd, C. A., Hatzenbuhler, N. T., Shea, M. H., Nuif, S. C. and Geory, T. G. (1991) Mol. Biochem. Parasitol. 48, 17–26). (The 74% figure is also produced by providing gaps in the amino acid sequence). The degree of amino acid sequence similarity between the trematode PFK from *Schistosoma mansoni* and PFK from the nematode *H. contortus* is no higher than with the human PFK.

Example 3

Construction of Recombinant Baculovirus with *Schistosoma mansoni* PFK and Transfection of Insect Cells.

The 5' untranslated region of PFK cDNA of pSm-PFK was truncated by PCR technique and subcloned into the BamHI site of pVL 1393, from Invitrogen (San Diego). The recombinant transfer vector, designated as pVL93 PFK, was cotransfected with linear baculovirus DNA (Acβ-gal) (obtained from T.S.F. Wang, Stanford University), into *Spodoptera frugiperda* (Sf9) insect cells (obtained from T. S. F. Wang, Stanford University) according to the procedure of Summers and Smith (Summers, M. D. and Sraith, G. E. (1987) Texas Agric. Exp. Stn. Bull. 1555, 1–56) and of Copeland and Wang (Copeland, W. C. and Wang, T. S. F. (1993) J. Biol. Chem. 268, 11028–11040).

To test for expression of PFK activity, PFK was isolated from insect cells infected with an expression vector containing a Sm-PFK polynucleotide. Isolated Sm-PFK protein was assayed for PFK activity and trematode PFK antigenic sites. A cell-free extract of the infected cells was prepared by sonication for 10 s (3 times for a total of 30 s) in a solution containing 50 mM Tris/1 mM EDTA, pH 8.0/1 mM phenylmethylsulfonyl fluoride. The sonicated extract was centrifuged for 10 min at 16,000×g. The supernatant fluid was used for phosphofructokinase assays as well as immunoblotting analysis. Rabbit antiserum prepared against purified PFK from *Fasciola hepatica*, another trematode was used (Kamemoto, E. S. and Mansour, T. E. (1986) J. Biol. Chem. 261, 4346–4351). Enzyme activity of PFK was determined in cell extracts by coupling with aldolase, triosephosphate isomerase and α-glycerophosphate dehydrogenase. NADH oxidation in the assay mixture was determined spectrophotometrically (Choate, G. L., Lan, L. and Mansour, T. E. (1985) J. Biol. Chem. 260, 4815–4822).

Two positive recombinant viruses were identified by visual observation of plaques, isolated from the infected cells. These recombinant viruses were used to express the enzyme by infecting other insect cells. After 48 h of infection, expression of PFK in extracts of the virus-infected Sf9 cells was examined by immuno-blotting and enzyme assays. Antisemro raised against PFK purified from the liver fluke *Fasciola hepatica*, another trematode (Kamemoto, E. S. and Mansour, T. E. (1986) J. Biol. Chem. 261, 4346–4351), was used for the immunoblot tests. The antiserum did not cross-react with human heart muscle or insect PFK. Extracts of infected cells were prepared as described herein. A single 86 kDa band was detected in extracts from recombinant virus clones of the infected cells (FIG. 1, lane R) but not in extract of control cells that were infected with only Acβ-gal virus (FIG. 1, lane C). Extracts of male (FIG. 1, lane M), and male and female (FIG. 1, lane M/F) schistosomes gave a similar band at 86 kDa, plus an additional 95 kDa band. The 86 kDa band represents the schistosome immuno-specific phosphofructokinase polypeptide. The 95 kDa band may represent a non-specific interaction between the polyclonal antisemro for the *F. hepatica* PFK and *S. mansoni* protein.

Functional demonstration of recombinant PFK was obtained by phosphofructokinase assays of control and infected cells. Table 1 shows that the recombinant virus-infected cell lysate has 24-fold more enzyme activity than the lysate of the control cells infected with Acβ-gal virus.

TABLE 1

Enzyme activity of recombinant phosphofructokinase in insect cells (SF9)

| SF9 cells | PFK activity (milliunits) per mg of protein |
|---|---|
| non-infected | 30 |
| Acβ-gal-infected (control) | 40 |
| Recombinant PFK in clone A (infected) | 930 |
| Recombinant PFK in clone B (infected) | 950 |

Cells extracts were prepared as described herein. Phosphofructokinase activity were assayed spectrophotometrically as previously described (Choate, G. L., Lan, L. and Mansour, T. E. (1985). J. Biol. Chem. 260, 4815–4822). One milliunit equals 1 micromole of product per milligram of protein.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. An isolated polynucleotide comprising:
   (a) a nucleic acid sequence at least 12 bases long and having at least 95% sequence identity with SEQUENCE ID NO: 1, which is capable of hybridizing with the complement of SEQUENCE ID NO: 1 under low stringency conditions, or
   (b) a nucleic acid sequence complementary to the sequence of (a).

2. The isolated polynucleotide of claim 1 wherein said nucleic acid sequence is a naturally occurring nucleic acid sequence.

3. The isolated polynucleotide of claim 2 wherein said nucleic acid sequence has the sequence of SEQUENCE ID NO: 1.

4. The isolated polynucleotide of claim 2 wherein said polynucleotide comprises a fragment of SEQUENCE ID NO: 1 and is at least 12 bases in length and which will hybridize to Schistosoma nucleic acids encoding phosphofructokinase.

5. The isolated polynucleotide of claim 4 wherein said fragment is at least 18 bases in length.

6. The isolated polynucleotide of claim 5 wherein said oligonucleotide has a nucleic acid sequence selected from a region of said SEQUENCE ID NO: 1 that does not encode a fructose-6-phosphate binding site or ATP binding site of Sm-PFK.

7. The isolated polynucleotide of claim 5 wherein said fragment is an oligonucleotide 20 bases or greater in length.

8. The isolated polynucleotide of claim 1 wherein said polynucleotide is 40 bases or greater in length.

9. The isolated polynucleotide of claim 8 wherein said nucleic acid sequence is identical to SEQUENCE ID NO: 1.

10. The isolated polynucleotide of claim 1 wherein said nucleic acid sequence is complementary to the sequence of SEQUENCE ID NO: 1.

11. The isolated polynucleotide of claim 10 wherein said polynucleotide comprises a fragment complementary to SEQUENCE ID NO: 1 and is at least 12 bases in length and which will hybridize to Schistosoma nucleic acids encoding phosphofructokinase.

12. The isolated polynucleotide of claim 11 wherein said polynucleotide has a nucleic acid sequence selected from a region of said SEQUENCE ID NO: 1 that does not encode a fructose-6-phosphate binding site or ATP binding site of Sm-PFK.

13. The isolated polynucleotide of claim 11 wherein said fragment is at least 18 bases in length.

14. The isolated polynucleotide of claim 13 wherein said fragment is an oligonucleotide 20 bases or greater in length.

15. The isolated polynucleotide of claim 14 wherein said oligonucleotide is 40 bases or greater in length.

16. The isolated polynucleotide of claim 15 wherein said nucleic acid sequence is identical to SEQUENCE ID NO: 1.

17. The isolated polynucleotide of claim 11 wherein said nucleic acid sequence includes an ATG translation intiation codon.

18. An isolated polynucleotide of claim 11 wherein said isolated polynucleotide is an oligonucleotide 12 to 40 bases in length.

19. The isolated polynucleotide of claim 1 wherein said nucleic acid sequence encodes a protein with the amino acid sequence of SEQUENCE ID NO: 2.

20. A method for producing phosphofructokinase, comprising:
  (a) culturing a cell transformed with an expression vector comprising said polynucleotide of claim 2, wherein said vector contains control sequences for expression that are compatible with said cell, under conditions that allow expression of said polynucleotide, and
  (b) isolating the phosphofructokinase produced in (a).

21. The method for producing phosphofructokinase of claim 20 wherein said cell is an *E. coli* cell.

* * * * *